US012291733B2

(12) United States Patent
Sathe et al.

(10) Patent No.: US 12,291,733 B2
(45) Date of Patent: May 6, 2025

(54) PROCESS FOR THE PREPARATION OF RECOMBINANT LECTIN PROTEIN

(71) Applicant: Unichem Laboratories Ltd, Maharashtra (IN)

(72) Inventors: Dhananjay Sathe, Maharashtra (IN); Sudeep Kumar, Gujarat (IN); Mamata Katdare, Maharashtra (IN)

(73) Assignee: Unichem Laboratories Ltd, Maharashtra (IN)

( * ) Notice: Subject to any disclaimer, the term of this patent is extended or adjusted under 35 U.S.C. 154(b) by 1055 days.

(21) Appl. No.: 17/273,044

(22) PCT Filed: Sep. 5, 2019

(86) PCT No.: PCT/IB2019/057471

§ 371 (c)(1), (2) Date: Mar. 3, 2021

(87) PCT Pub. No.: WO2020/074977
PCT Pub. Date: Apr. 16, 2020

(65) Prior Publication Data

US 2021/0324438 A1 Oct. 21, 2021

(30) Foreign Application Priority Data

Sep. 7, 2018 (IN) ............................ 201821008382
Jan. 14, 2019 (IN) ............................ 201921001559

(51) Int. Cl.
| | |
|---|---|
| *C12P 21/02* | (2006.01) |
| *B01D 15/32* | (2006.01) |
| *B01D 15/36* | (2006.01) |
| *C07K 1/18* | (2006.01) |
| *C07K 1/20* | (2006.01) |
| *C07K 1/34* | (2006.01) |
| *C07K 1/36* | (2006.01) |
| *C07K 14/42* | (2006.01) |
| *C07K 14/47* | (2006.01) |

(52) U.S. Cl.
CPC ............ *C12P 21/02* (2013.01); *B01D 15/327* (2013.01); *B01D 15/362* (2013.01); *B01D 15/363* (2013.01); *C07K 1/18* (2013.01); *C07K 1/20* (2013.01); *C07K 1/34* (2013.01); *C07K 1/36* (2013.01); *C07K 14/42* (2013.01); *C07K 14/4726* (2013.01)

(58) Field of Classification Search
CPC ..... C12P 21/02; B01D 15/327; B01D 15/362; B01D 15/363; C07K 1/18; C07K 1/20; C07K 1/34; C07K 1/36; C07K 14/42; C07K 14/4726; C07K 1/16; C12N 15/70
See application file for complete search history.

(56) References Cited

FOREIGN PATENT DOCUMENTS

| | | | | |
|---|---|---|---|---|
| CN | 1483816 A * | 3/2004 | ............. | C07K 14/42 |
| WO | WO 2010095143 A2 * | 8/2010 | | |

OTHER PUBLICATIONS

Caglar et al. The *E. coli* molecular phenotype under different growth conditions, 2017, Nature Scientific Reports, 7:45303 (Year: 2017).*
Chen et al.Impact of carbon and nitrogen conditions on *E. coli* surface thermodynamics, 2003, Colloids and Surfaces B: Biointerfaces, 28: 135-146 (Year: 2003).*
Brown et al.Scale-up of microbial fermentation using recombinant *E. coli* in HyPerforma 30 L and 300 L Single-Use Fermentors, 2016, Thermoscientific Application Notes, pp. 1-5 (Year: 2016).*
Ginsey et al., Tuning of the Carbon-to-Nitrogen Ratio for the Production of L-Arginine by *Escherichia coli*. Fermentation, 2017, vol. 3, 60; doi:10.3390, pp. 1-11 (Year: 2017).*
Ou et al., Stationary phase protein overproduction is a fundamental capability of *Escherichia coli*. Biochem. Biophys. Res. Commun., 2004, vol. 314: 174-180. (Year: 2004).*
Peppa et al., Molecular Cloning, Carbohydrate Specificity and the Crystal Structure of Two Sclerotium rolfsii Lectin Variants. Molecules, 2015, vol. 20: 10485-10865. (Year: 2015).*
Leonidas et al., "Structural Basis for the Carbohydrate Recognition of the Sclerotium rolfsii Lectin", J Mol Biol (May 11, 2007; 368, pp. 1145-1161.

* cited by examiner

*Primary Examiner* — Ganapathirama Raghu
(74) *Attorney, Agent, or Firm* — BACON & THOMAS, PLLC

(57) ABSTRACT

The present invention relates to the process to prepare recombinant lectin having amino acid sequence of SEQ ID NO:1, wherein the process comprises fed-batch fermentation of a clone in a host cell at specific feeding rate with carbon to Nitrogen ratio of 3:1 to 6:1. The invention also relates to the process of purification of recombinant lectin having amino acid sequence of SEQ ID NO: 1.

13 Claims, 2 Drawing Sheets

Specification includes a Sequence Listing.

Fig 1. Annotated diagram of pET27b Vector with Sequence ID NO:5: Nucleotide Sequence Encoding Amino Acid Sequence of SEQ ID NO:1
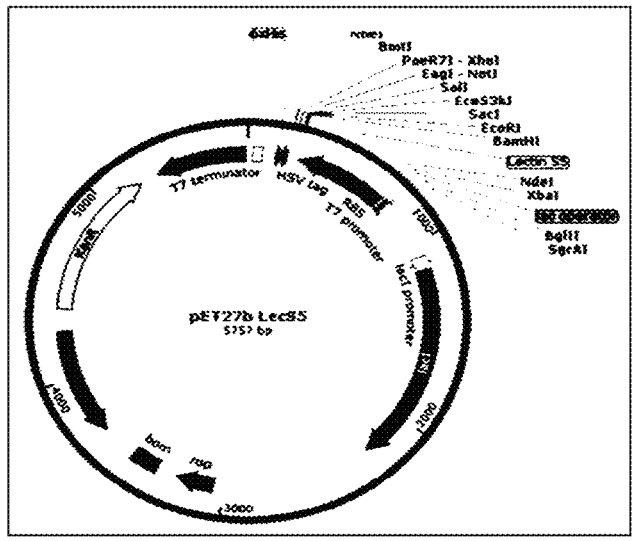
Fig 2. SDS-PAGE analysis of purified recombinant lectin amino acid sequence of SEQ ID NO:1
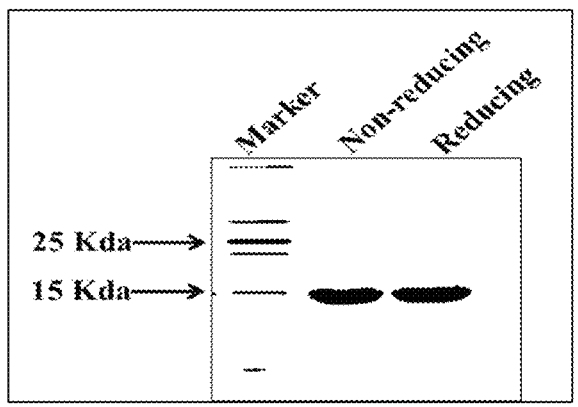

Fig 3. Western blot analysis of purified recombinant lectin amino acid sequence of SEQ ID NO: 1
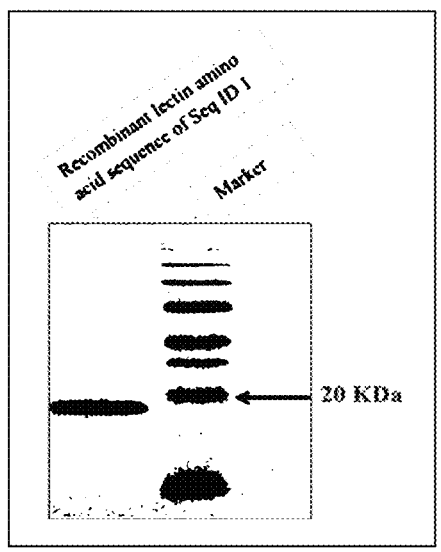

PROCESS FOR THE PREPARATION OF RECOMBINANT LECTIN PROTEIN

CROSS REFERENCE TO RELATED APPLICATIONS

This application claims the benefit of Indian Provisional Application No. 201821008382 filed on Sep. 7, 2018 and Indian Provisional Application No. 201921001559 filed on Jan. 14, 2019, the entire contents of which are incorporated herein by reference.

FIELD OF INVENTION

This invention relates to a recombinant lectin protein and a method of preparing a recombinant lectin protein. The invention also relates to a method of purifying a crude recombinant lectin protein.

BACKGROUND OF INVENTION

Lectins are carbohydrate-binding proteins, macromolecules that are highly specific for sugar moieties of other molecules. Lectins perform recognition on the cellular and molecular level and play numerous roles in biological recognition phenomena involving cells, carbohydrates, and proteins. They are divalent or polyvalent carbohydrate-binding proteins that bind and precipitate glycoproteins and agglutinate red blood cells. Lectins found in animals are most often found to aid in cell interactions, while plant lectins are known to ward off potential predators or pathogens. Some lectins can detect cancer-associated glycans and therefore have the potential to serve as biomarkers for malignant tumors and to assist in the study of changes in the glycosylation motif in cancer cell lines.

Purified lectins are important in a clinical setting because they are used for blood typing. Some of the glycolipids and glycoproteins on an individual's red blood cells can be identified by lectins. Many lectins are used as biomarkers indicating early detection of malignant growth or as autophagy inducers while other lectins also show the ability to inhibit cancerous growth through apoptosis. Due to unregulated cell proliferation, some of the carbohydrate moieties are expressed as an antigen on cancerous cells. Lectins are used as a drug delivery agent in cancer therapy because they bind specifically to the malignant tumours. Further since the lectins also modulate cancer associated pathways they have potential as cancer diagnostic and therapeutic agents.

There are several antigens to which lectins bind and which have been characterised on the cancer cell surface; most of the antigens are specific for a particular type of cancer and lectin-binding to these antigens can result in inhibition of cancerous growth through inducing apoptosis in the cancerous cells. Currently, most commercially available lectins are from plants and other eukaryotes.

*Sclerotium rolfsii* lectin (SRL) is a lectin that has been isolated from the sclerotial bodies of the soil-borne phytopathogenic fungus *S. rolfsii*. SRL has specificity towards Thomsen-Friedenreich (TF) antigen and Tn antigen. TF antigen is a disaccharide (Gal$\beta$1→3GalNAc-$\alpha$-Ser/Thr) that is overexpressed on the cell surface of various human cancer cells. Tn antigen is a monosaccharide (GalNAc-$\alpha$-). Due its specificity for TF and Tn antigen, SRL has been shown to bind to human colon cancer, ovarian cancer and leukaemic cells. The crystal structure of SRL has been determined (Leonidas et al., J Mol Biol. 2007 May 11; 368(4):1145-61).

Whilst the lectins offer many advantages as anti-cancer tools, they still carry with them many limitations such as a lack of selectivity, inconsistent quality and performance and the production not being readily scalable. Moreover, the plant-derived lectins have often been reported to bind to a range of different glycan structures and so lack the selectivity required for many applications. Also the batch-to-batch variability is common when using plant lectins. The quality of the products depends on the methodology of isolation of the plant material, and on the quality of the starting plant material itself.

Isolation of lectin from the natural sources is not reliable because the lectin so obtained lacks in consistency with respect to the desired properties. Further isolating proteins from natural sources is an expensive and difficult process. The techniques used to isolate the naturally occurring lectins usually provide very low yields especially if the protein is only present at low concentrations. Also they are occasionally unable to distinguish between isoforms of the same lectin. Therefore, they are obtained as mixtures, which provide a large range of uncertainty. In this sense, the production of recombinant lectins by recombinant DNA techniques has the advantage of providing single proteins, with better and consistent yields having precise characterisation in drastically less amount of time and at the same time being readily scalable. By using rDNA technology one can transfer the gene that produces the protein of interest into a suitable host. The protein then can be produced and isolated with less time and effort as compared with the traditional methods.

WO 2010/095143 discloses recombinant lectin variants Rec-2 and Rec-3, which are derived from the native SRL sequence by the substitution of 3 or 5 amino acids respectively. The crystal structure of these variants has been reported (Peppa et al., Molecules. 2015 Jun. 12; 20(6): 10848-65).

WO 2014/203261 discloses a recombinant lectin variant derived from the native SRL sequence by the substitution of 12 amino acids.

Indian application 350/MUM/2009 (PCT application WO 2010/095143) for the first time disclosed an amino acid sequence of SEQ ID NO: 1 (designated as SEQ ID 2 in 350/MUM/2009) derived from native amino acid sequence of SEQ ID NO:2 (designated as SEQ ID 1 in 350/MUM/2009) derived from fungus, *Sclerotium rolfsii*. WO 2010/095143 describes the laboratory scale production of recombinant lectins in *E. coli* cells, wherein the gene coding for the recombinant lectin is cloned into an expression vector. However, the method suffers from certain disadvantages, including difficulty in controlling the culture parameters, such as the amount of dissolved oxygen and pH, as well as lack of control over the protein expression. Further, the culture yields low cell mass and thus results in overall low yield of the purified protein. Moreover, the process is not industrially scalable.

The lectin with amino acid sequence of SEQ ID NO: 1 shows high stability and solubility as compared to native lectin derived from fungus *Sclerotium rolfsii* and exhibits-cancer cell binding properties. Lectins have a variety of uses in research, medicine and biochemical techniques. For example, the lectin having the amino acid sequence of SEQ ID NO: 1 has high pharmaceutical potential. There is therefore need to devise a process for producing recombinant lectins that is higher yielding, more cost effective, more easily scaleable and/or having improved efficiency.

The present invention has been devised with these issues in mind.

OBJECT OF INVENTION

The main object of the present invention is to overcome the disadvantages of prior art references and devise a highly efficient process to prepare the amino acid sequence of SEQ ID NO:1.

Another object of the invention is to provide a process which is high yielding and cost effective and which can be performed using easily available raw material. Yet another object of the invention is to provide an easily scaleable process to prepare the amino acid sequence of SEQ ID NO:1.

Another object of the present invention is to provide a process that yields amino acid sequence of SEQ ID NO:1 in a highly pure form.

SUMMARY OF INVENTION

In one aspect of the present invention there is provided a method of preparing a recombinant lectin protein, the method comprising expressing a recombinant lectin protein encoded by a recombinant lectin gene in a host cell in culture, wherein expression is performed under conditions for the cell such that the cell has a doubling time of no more than 160 minutes. In some embodiments, the expression is performed under conditions for the cell such that the cell has a doubling time of at least 100 minutes.

In one embodiment, the method comprises expressing a recombinant lectin protein encoded by a recombinant lectin gene in a host cell in culture at a temperature of no more than 22° C. In a further embodiment, the expression is performed at a temperature of at least 15° C. and no more than 22° C.

In some embodiments, the host cell for expression of recombinant lectin is E. coli. In some embodiments, the recombinant lectin protein is selected from SEQ ID NO:1, SEQ ID NO:3, SEQ ID NO:4, or an amino acid sequence having at least 60%, 70%, 80%, 90%, 95%, 97%, 98%, or 99% homology with any of these sequences.

In some embodiments, the host cell culture has a volume of at least 10 L.

In some embodiments, the method comprises culturing the host cell, said culturing comprising: a growth phase during which the host cell is grown prior to protein expression; and an expression phase during which protein expression is performed. In further embodiments, the growth phase is carried out at a temperature which is greater than the temperature at which the expression phase is performed. In further still embodiments, the temperature is reduced from the growth phase to the expression phase over a period of at least 4 and no more than 7 hours.

In some embodiments, the expression phase is induced by addition of inducer at a concentration of at least 0.1 mM and no more than 0.7 mM. In other embodiments, the inducer is added to the culture at a concentration of no more than 0.5 mM. In further still embodiments, the expression phase is induced by addition of inducer when the optical density of the culture is at least 25 and no more than 40.

In some embodiments, the method comprises an expression phase induced by addition of an inducer when the optical density of the culture is at least 25 and no more than 40, wherein the inducer added is at a concentration of at least 0.1 mM and no more than 0.7 mM.

In another aspect of the present invention there is provided a method of culturing a host cell, wherein the expression phase is induced by addition of inducer at a concentration of at least 0.1 mM and no more than 0.7 mM and wherein expression is performed under conditions for the cell such that the cell has a doubling time of no more than 160 minutes. In some embodiments, the inducer is added to the culture at a concentration of no more than 0.5 mM.

In a further aspect of the present invention there is provided a method of culturing a host cell, wherein the expression phase is induced by addition of inducer when the optical density of the culture is at least 25 and no more than 40 and wherein expression is performed under conditions for the cell such that the cell has a doubling time of no more than 160 minutes.

In some embodiments, the recombinant lectin protein is selected from SEQ ID NO:1, SEQ ID NO:3, SEQ ID NO:4, or an amino acid sequence having at least 60%, 70%, 80%, 90%, 95%, 97%, 98%, or 99% homology with any of these sequences.

In certain embodiments, the optical density is the measure of the population of the host cell in culture and is measured at 600 nm.

In some embodiments, the inducer is IPTG.

The present invention also provides a method of preparing a recombinant lectin protein, the method comprising expressing a recombinant lectin protein encoded by a recombinant lectin gene in a host cell in culture, wherein expression is performed under conditions for the cell such that the cell has a doubling time of no more than 160 minutes and wherein the host cell culture has a volume of at least 10 L.

In another aspect of the present invention, there is provided a process to prepare recombinant lectin, wherein the process comprises:

a) optionally, cloning a recombinant lectin gene into an expression vector and inserting the expression vector into a host cell;

b) culturing the host cell in a suitable medium, wherein said culturing comprises a growth phase which is carried out at a temperature of from 25° C. to 40° C., and an expression phase during which the recombinant lectin protein encoded by the recombinant lectin gene is expressed, wherein the expression phase is carried out at a temperature of from 15° C. to 30° C. and wherein the carbon to nitrogen ratio is maintained during the expression phase at from 3:1 to 6:1;

c) optionally, isolating the recombinant lectin protein expressed in (b) to obtain a crude recombinant lectin protein; and d) optionally, purifying the crude recombinant lectin protein to obtain a recombinant lectin protein isolate.

In one embodiment, the expression vector in step a) is as depicted in FIG. 1. In another embodiment, in step 'b' the carbon source is added to the culture at a rate of at least 0.5 $gL^{-1} h^{-1}$ and at a rate of no more than 2 $gL^{-1} h^{-1}$ during the induction phase, wherein the carbon source is glucose or glycerol. Alternatively, in step 'b' the nitrogen source is added to the culture at a rate of at least 0.4 $gL^{-1} h^{-1}$ and at a rate of no more than 1.5 $gL^{-1} h^{-1}$ during the induction phase, wherein the nitrogen source is tryptone, peptone or yeast extract.

In another embodiment, isolating a crude recombinant lectin protein in step 'c' is carried out by centrifugation followed by disruption of cell surface. In a further embodiment, purifying the crude recombinant lectin protein in step 'd' comprises at least one chormatographic step. In a further embodiment, the at least one chromatographic step comprises anion exchange chromatography and/or cation exchange chromatography. Alternatively the at least one chromatographic step comprises hydrophobic interaction chromatography. In an additional embodiment, purifying the crude recombinant lectin protein in step 'd' comprises a filtration step.

In some embodiments, the recombinant lectin protein is selected from SEQ ID NO:1, SEQ ID NO:3, SEQ ID NO:4, or an amino acid sequence having at least 60%, 70%, 80%, 90%, 95%, 97%, 98%, or 99% homology with any of these sequences. In some embodiments, the host cell culture has a volume of at least 10 L.

In yet another aspect of the present invention, there is provided a method of purification of crude recombinant lectin protein, wherein the process comprises:
a) initial purification of the crude recombinant lectin protein by anion exchange chromatography to obtain a first purified elute;
b) optional purification of the first purified elute by hydrophobic interaction chromatography to obtain a second purified elute;
c) optional purification of the second purified elute by cation exchange chromatography to obtain a third purified elute;
d) further purification of the second or third purified elute by anion exchange chromatography to obtain a fourth purified elute; and
e) buffer exchange of the fourth purified elute by diafiltration to obtain a purified recombinant lectin protein isolate.

In some embodiments, the crude recombinant lectin protein is obtained by the methods described above. In some embodiments, the recombinant lectin protein is selected from SEQ ID NO:1, SEQ ID NO:3, SEQ ID NO:4, or an amino acid sequence having at least 60%, 70%, 80%, 90%, 95%, 97%, 98%, or 99% homology with any of these sequences.

In some embodiments, the host cell culture has a volume of at least 10 L.

In a further aspect of the present invention, there is provided a recombinant lectin protein produced by the methods described above.

In another aspect of the present invention, there is provided a method for preparing recombinant lectin protein having less than 20% of recombinant lectin with initiator methionine, wherein the method comprises at least one of the following conditions:
a) an expression temperature of at least 15° C. and no more than 22° C.;
b) the expression (i.e. induction) phase is carried out for at least 10 hours;
c) carbon source is added to the culture at a rate of from 0.5 to 2 $gL^{-1} h^{-1}$;
d) the nitrogen source is added to the culture at a rate of from 0.4 to 1.5 $gL^{-1} h^{-1}$;
e) an inducer concentration of at least 0.1 mM and no more than 0.5 mM;
f) purifying the crude recombinant lectin protein using at least one chromatography step.

In a final aspect of the present invention, there is provided a recombinant lectin protein having less than 20% of recombinant lectin with initiator methionine. That is to say, there is provided a recombinant lectin protein mixture wherein less than 20% of the recombinant lectin protein polymers have initiator methionine. In specific embodiments the lectin protein polymers are in other respects in accordance with the other aspects of the present invention. The invention further provides recombinant lectin protein prepared by the methods of the present invention. Specifically it provides recombinant lectin protein having less than 20% of recombinant lectin with initiator methionine.

BRIEF DESCRIPTION OF FIGURES AND TABLES

FIG. 1. Annotated diagram of pET27b Vector with nucleotide sequence of SEQ ID NO:5 encoding amino acid sequence of SEQ ID NO:1.
FIG. 2. SDS-PAGE analysis of purified recombinant lectin having amino acid sequence of SEQ ID NO:1.
FIG. 3. Western blot analysis of purified recombinant lectin having amino acid sequence of SEQ ID NO:1.
Table 1. Analysis of proportion of methionine lectin obtained from different fermentation conditions.
Table 2. Doubling time of *E. coli* at different fermentation conditions.

DETAILED DESCRIPTION OF THE INVENTION

The term "doubling time" as used herein refers to the period of time required for the cell to double in number, for example, for one cell to multiply into two cells, or for a cell population to double in number. As the skilled person will appreciate, doubling time can be calculated by dividing the natural logarithm of two by the exponent of growth.

Reference to a "recombinant" product, as used herein, refers to a genetically engineered product. It will be appreciated that genetic engineering is the non-natural manipulation of genes. Thus a recombinant product is a product which exists or is synthesised in a non-natural environment such as a host cell in which the product is not present in nature. The term "protein" as used herein refers to a polymer of amino acid residues.

In the context of the present invention, the term "growth phase" will be understood to refer to a period of culture wherein the host cells are grown to a desired population density.

The term "expression phase" as used herein, will be understood to refer to a period of culture during which recombinant lectin is expressed from the host cell. It will be appreciated that the expression phase may be distinguished from the growth phase by increased expression in the expression phase relative to the growth phase.

The term "lectin" as used herein refers to a carbohydrate-binding protein.

The term "amino acid" as used herein refers to naturally occurring and synthetic amino acids, as well as amino acid analogues and amino acid mimetics that have a function that is similar to the naturally occurring amino acids. Naturally occurring amino acids are those encoded by the genetic code and include the proteinogenic amino acids. Naturally occurring amino acids also include those modified after translation in cells. Synthetic amino acids include non-canonical amino acids such as selenocysteine and pyrrolysine. Typically synthetic amino acids are not proteinogenic amino acids.

The terms "homology" or "homologous" as used herein refer to two or more referenced entities that share at least partial identity over a given region or portion. Areas, regions or domains of homology or identity refer to a portion of two or more referenced entities that share homology or identity or are the same.

Thus, where two sequences are identical over one or more sequence regions they share identity in these regions. Substantial homology refers to a molecule that is structurally or functionally conserved such that it has or is predicted to have at least partial structure or function of one or more of the structures or functions (e.g., a biological function or activity) of the reference molecule, or a relevant/corresponding region or portion of the reference molecule to which it shares homology.

According to a first aspect of the invention, there is provided a method of preparing a recombinant lectin protein, the method comprising:

expressing a recombinant lectin protein encoded by a recombinant lectin gene in a host cell in culture, wherein expression is performed under conditions for the cell such that the cell has a doubling time of no more than 160 minutes.

In some embodiments, the recombinant lectin gene is not a naturally occurring gene. The recombinant lectin protein may not have the amino acid sequence of a naturally occurring lectin protein. For example, the recombinant lectin protein may not comprise or consist of the amino acid sequence of SEQ ID NO:2.

In some embodiments, expression is performed under conditions for the cell such that the cell has a doubling time of at least 100 minutes.

The present inventors have found that by expressing the recombinant lectin protein under culture conditions which limit the doubling time of the host cell, a higher level of soluble protein is obtained. Furthermore, such expression conditions has also been found to lead to improved cleavage of the initiator methionine from the recombinant lectin, leading to an increased yield of the protein which lacks the initiator methionine. By providing a process which results in the production of an increased amount of soluble protein from which the methionine has already been cleaved, this reduces the need for downstream processing of the protein, which would be necessary if a significant proportion of the protein was expressed as insoluble inclusion bodies. This reduces the complexity of the process, improves efficiency, and makes the process more economically viable.

The term "soluble" as used herein refers to the modified lectin protein being expressed in a soluble or at least partially soluble form. In one embodiment, solubility of the modified lectin protein is determined by cell lysis of a host cell that expresses the modified lectin protein and subsequent SDS-PAGE analysis of the lysis supernatant and pellet. The presence of the modified lectin protein in the lysis supernatant indicates that it is soluble. The presence of the modified lectin protein in the lysis supernatant and the pellet indicates that it is partially soluble. In one embodiment, the term "soluble" as used herein refers to the modified lectin protein not forming inclusion bodies. Using the method described above, the presence of the modified lectin protein in the pellet indicates that it is expressed as inclusion bodies.

The term "cleavage of an initiator methionine" as used herein refers to removal of the N-terminal (initiator) methionine from an amino acid sequence. In one embodiment, the cleavage of the initiator methionine is catalysed by the enzyme methionine aminopeptidase (MAP). In one embodiment, cleavage of the initiator methionine is determined using mass spectrometry analysis known to a person skilled in the art.

The term "improved cleavage of the initiator methionine" as used herein refers to an increase in the extent of initiator methionine cleavage relative to a control. In one embodiment, it refers to an at least 5%, 10%, 25%, or 50% increase in the extent of initiator methionine cleavage relative to a control. In one embodiment, the control is a lectin protein of SEQ ID NO: 2. In some embodiments, there is provided a recombinant lectin protein (i.e. a mixture of lectin protein polymers) having less than 50%, 40%, 30%, 20% or 10% of recombinant lectin with initiator methionine (i.e. met-lectin). Or in other words, the method of the invention enables the production of at least 50%, 60%, 70%, 80% or at 90% methionine-free recombinant lectin protein (i.e. protein lacking the initiator methionine residue). It will be appreciated that the doubling time of the host cell will be influenced by a number of factors, such as the culture temperature, the culture medium, feeding rate of nutrients and the type of host cell. It will be within the capabilities of the skilled person to vary one or more of these parameters in order to achieve a desired doubling rate.

One of the parameters which can be used to control the doubling time of the host cell is the temperature at which expression is carried out. In some embodiments, expression of the recombinant lectin is carried out at a temperature of no more than 30° C., no more than 25° C., no more than 22° C., no more than 21° C., no more than 20° C., no more than 19° C. or no more than 18° C.

In some embodiments, expression of the recombinant lectin is carried out at a temperature (also referred to herein as the "expression temperature") of at least 15° C., at least 16° C. or at least 17° C. In some embodiments, the expression temperature is 18° C.

Carrying out protein expression at temperatures below 25° C., such as 18° C., has been found to be particularly advantageous since it helps to minimise the amount of protein produced which comprises the initiator methionine residue. This is particularly the case when the host cell is a mesophile, such as E. coli. The fact that expression at lower temperatures such as around 18° C. is beneficial is particularly surprising, since it is far below the optimum growth temperature of host cells commonly used for recombinant protein expression, like E. coli.

As is known in the art, the temperature of the host cell culture can be controlled by placing the culture, for example in a flask or bioreactor, in an environment having the desired temperature, such as in a water-bath or temperature-controlled room or chamber.

Prior to expression of the recombinant lectin protein, the host cells may be grown in culture to a desired population density. Thus, in some embodiments, the method comprises culturing the host cell, said culturing comprising:
 a growth phase during which the host cells are grown prior to protein expression; and
 an expression phase during which protein expression is performed.

During the growth phase, it may be desirable to cause the host cells to multiply quickly, in order to maximise protein production during the subsequent expression phase. In the growth phase the doubling time of the host cells may be lower than the doubling time in the expression phase (i.e. the cells are multiplying faster in the growth phase). For example, doubling time of the host cells in the growth phase may be no more than 100 minutes. It will be appreciated that the doubling time of the cells within the growth phase will vary depending on whether the cells are in the lag phase of growth, during which doubling time is relatively long, or the exponential phase during which the doubling time is relatively short.

In some embodiments, the growth phase is carried out at a temperature which is greater than the temperature at which the expression phase is performed. In some embodiments, the growth phase, or at least a portion thereof, is carried out at a temperature of at least 25° C., at least 30° C. or at least 35° C. In some embodiments, the growth phase, or a portion thereof, is carried out at a temperature of no more than 40° C., or no more than 38° C.

It will therefore be appreciated that in some embodiments the method comprises reducing the temperature of culture from the growth phase to the expression phase. The temperature may be reduced gradually over a period of a few hours. For example, the temperature may be reduced over a period of at least 2 hours, at least 4 hours or at least 6 hours. In some embodiments, the temperature is reduced over a period of no more than 6 or 7 hours.

The temperature may be reduced during the growth phase. For example, in a first stage the growth phase may be carried out at a first temperature (e.g. 30° C.), and in a second stage of the growth phase the temperature may be reduced to the temperature of the expression phase (e.g. a reduction of from 30° C. to 18° C.).

Expression of the recombinant lectin protein may be initiated by the addition of an inducer to the culture. Thus, the expression phase may be defined as the stage during which the host cell culture comprises the inducer. This phase may also be referred to as the "induction phase".

As is known in the art, an inducer is a molecule that regulates gene expression. The recombinant lectin gene may be under the control of an operator sequence. In the absence of the inducer, gene expression may be prevented by the binding of a repressor to the operator sequence, or alternatively by the lack of activation by an activator. In the presence of the inducer, repression of gene expression may be prevented, or activation of gene expression may be enabled. Therefore, by placing the recombinant lectin gene under the control of an inducer-regulated operator sequence, the expression of the recombinant lectin protein can be tightly controlled such that "leaky" expression is avoided. Well known examples of inducible expression systems include the ara operon and the lac operon. In the lac operon, binding of a repressor to the lac operator prevents transcription of downstream genes. Protein expression can be initiated by using allolactose or its mimic IPTG (Isopropyl β-D-1-thiogalactopyranoside), which binds to the lac repressor and releases it from the lac operator, thereby allowing the transcription of genes within the operon. Other inducible operons will be known to those skilled in the art.

Thus, in some embodiments, the recombinant lectin gene is under the control of the lac operator. In such embodiments, the inducer comprises IPTG.

IPTG may be added to the culture at a concentration of at least 0.1 mM, at least 0.2 mM or at least 0.25 mM.

In some embodiments, the concentration of IPTG is less than 1 mM. The concentration of the IPTG may be no more than 0.7 mM, or no more than 0.5 mM. The use of a lower concentration of the IPTG may be advantageous to maintain low expression levels, which is thought to assist with efficient cleavage of the initiator methionine.

The inducer may be added once the population of host cells has increased to a desired density during the growth phase. The population of the host cells can be determined by measuring the optical density (OD) of the culture. In some embodiments, the inducer is added (i.e. the expression phase is initiated) when the OD600 (the optical density of the culture measured at 600 nm) is at least 25, at least 30, at least 35, at least 38 or at least 40. In some embodiments, the inducer is added when the OD600 is at least 25 and no more than 40.

As is commonly known in the art, in batch culture cells are grown initially to obtain a desired cell mass. During this phase, the focus is on the amplification of cell growth rather than on recombinant protein synthesis. In general, the timing of induction is decided by the period when the desired cell mass is in active growth, during which the cells have the maximum number of ribosomes for protein synthesis. After obtaining the desired cell mass, the recombinant protein will be produced after addition of the inducer. Hence, the timing of induction is important for productivity of the recombinant protein. The timing of induction will vary depending on factors such as the type of host cell, the type of culture media, the culture conditions and the type of recombinant protein.

In some embodiments, the growth phase is carried out for at least 4 hours, at least 6 hours, at least 8 hours or at least nine hours, prior to addition of the inducer which initiates the expression phase.

The expression phase (i.e. the culture time after addition of the inducer) may be at least 10 hours, at least 12 hours, at least 16 hours, at least 20 hours, at least 24 hours, at least 30 hours or at least 35 hours. In some embodiments the expression phase is carried out for up to 40 hours.

A longer expression phase is particularly beneficial when expression is carried out at lower temperatures, since the growth rate of the cells is slow and thus the doubling time is greater. Thus, the time allowed for the expression phase is extended to support more cell growth and compensate for the lower growth rate due to the lower temperature.

Without being bound by theory, it is believed that a longer expression (induction) phase and a prolonged doubling time enables a steady increase in the amount of protein being expressed. Due to the metabolic conditions within the host cell, there is sufficient time for cleavage of the initiator methionine by methionine amino peptidase (MAP), thereby helping to maximise the yield of methionine-free recombinant protein.

It will be appreciated that the skilled person will be able to select suitable culture conditions for a given host cell, including suitable culture media containing necessary nutrients to support the growth of the cells and protein expression. In some embodiments, the cells are cultured in liquid media. Suitable liquid media for culturing microbial cells includes lysogeny/luria broth (LB).

It is preferred that the ratio of carbon to nitrogen in the culture medium is maintained at a level of from 3:1 to 6:1. This ratio can be maintained by controlling the feeding rate of the culture.

The requirement of nutrients which are required for cell growth and protein expression will be determined at least in part by factors such as the population density of the cells, the culture temperature, the amount of inducer and the desired rate of protein expression. The rate of feeding nutrients to the cells may therefore be used to help control the growth rate, and thus the rate of protein expression.

In some embodiments, a carbon source is added to the culture at a rate of no more than 2 $gL^{-1}$ $h^{-1}$, or no more than 1.5 $gL^{-1}$ $h^{-1}$ during the expression phase. The carbon source may be added at a rate of at least 0.5 $gL^{-1}$ $h^{-1}$, or at least 0.8 $gL^{-1}$ $h^{-1}$ during expression.

The carbon source may comprise or consist of glycerol. Additionally or alternatively, other carbon sources such as glucose or dextrose may be used.

In some embodiments, a nitrogen source is added to the culture at a rate of no more than 1.5 $gL^{-1}$ $h^{-1}$, or no more than 1 $gL^{-1}$ $h^{-1}$ during the expression phase. The nitrogen source may be added at a rate of at least 0.4 $gL^{-1}$ $h^{-1}$ or at least 0.6 $gL^{-1}$ $h^{-1}$ during protein expression.

It has been found that by limiting the supply of carbon and/or nitrogen to within the parameters identified above, the rate of cell growth and protein expression is optimized such that the protein is substantially expressed in soluble form and with the majority of the protein lacking the initator methionine. Conversely, uncontrolled feeding has been found to lead to an increased rate of protein expression and incomplete methionine cleavage.

In some embodiments, the method of the invention enables the production of at least 80%, at least 85% or at least 90% of methionine-free recombinant lectin protein (i.e. protein lacking the initiator methionine residue).

In some embodiments, the method comprises one or more, or all, of the following conditions:
an expression temperature of at least 15° C. and no more than 22° C. (e.g. 18° C.);
the expression (i.e.induction) phase is carried out for at least 10 hours;
carbon source is added to the culture at a rate of from 0.5 to 2 $gL^{-1}$ $h^{-1}$;
the nitrogen source is added to the culture at a rate of from 0.4 to 1.5 $gL^{-1}$ $h^{-1}$;
an inducer concentration of at least 0.1 mM and no more than 0.5 mM.

The carbon and/or nitrogen source may be added to the culture during the expression phase, the growth phase or during the expression and the growth phases.

In some embodiments, the recombinant lectin protein is altered at at least one of amino acid positions 1, 14, 34, 113 and 123 of the native SRL amino acid sequence (SEQ ID NO: 2) as described in WO2010/095143, which incorporated herein by reference. In some embodiments, the recombinant lectin protein is altered at all of these positions relative to the native SRL.

The recombinant lectin protein may comprise or consist of an amino acid sequence selected from:
(i) SEQ ID NO:1;
(ii) SEQ ID NO: 3;
(iii) SEQ ID NO: 4; or
(iv) an amino acid sequence having at least 60%, at least 70%, at least 80%, at least 90%, at least 95%, at least 97%, at least 98% or at least 99% homology with SEQ ID NO:1, 3 or 4.

SEQ ID NO: 1 represents a variant of the *S. rolfsii* lectin amino acid sequence (reported as Rec-2 in WO 2010/095143).

SEQ ID NO: 2 represents the native *S. rolfsii* lectin amino acid sequence.

SEQ ID NO: 3: represents a variant of the *S. rolfsii* lectin amino acid sequence (reported as Rec-3 in WO 2010/095143).

SEQ ID NO: 4: represents a variant of the *S. rolfsii* lectin amino acid sequence (reported in WO 2014/203261).

In one embodiment, the percentage "homology" between two sequences is determined using the BLASTP algorithm with default parameters (Altschul et al. Nucleic Acids Res. 1997 Sep. 1; 25 (17): 3389-402). In particular, the BLAST algorithm can be accessed on the internet using the URL: https://blast.nebi.nlm.nih.gov/Blast.egi_blast.ncbi.nlm.nih-.gov/Blast.cgi. In an alternative embodiment, for global sequence alignments, percentage identity homology between two sequences is determined using the EMBOSS Needle algorithm using default parameters. In particular, the EMBOSS Needle algorithm can be accessed on the internet using the URL:
[www.]ebi.ac.uk/Tools/psa/emboss needle/.

Unless otherwise indicated, the term "homology" is used interchangeably with the term "identity" in the present specification.

The recombinant lectin gene may comprise or consist of a nucleotide sequence according to SEQ ID NO: 5. However, it will be appreciated that due to the degeneracy of the genetic code, there are many alternative nucleotide sequences that can give rise to the same amino acid sequence.

In some embodiments, the recombinant lectin gene is comprised within an expression construct, such as a plasmid or vector. The expression construct may further comprise a selectable marker which enables the selection of host cells carring the construct encoding the recombinant lectin gene. The selectable marker may be an antibiotic, such as kanamycin. In such embodiments, the culture medium may further comprise an antibiotic.

Suitable artificial plasmids for gene expression in bacterial cells include pET vectors, although other expression vectors will be known to the skilled person. In some embodiment, the vector is pET27b.

In some embodiments the host cell culture has a volume of at least 10 litres (L), at least 20 L, at least 30 L, at least 40 L, at least 50 L or at least 100 L. Expression may be carried out in an industrial fermenter.

In some embodiments, the method further comprises a step of cloning a recombinant lectin gene (e.g. a gene comprising the sequence of SEQ ID NO: 5) into an expression vector. Molecular cloning techniques will be known to the skilled person, and are described in textbooks such as "Molecular Cloning: A Laboratory Manual" by Sambrook and Russell.

The host cells may be microbial cells, such as a bacteria, archaea, yeast or fungi. In some embodiments the host cell is a bacterium, such as *E. coli*. A particularly preferred strain is *E. coli* BL21 DE3 Gold.

In some embodiments, the method further comprises a step of inserting the expression vector into the host cell. This may be achieved using methods that are commonly known to those skilled in the art, such as transformation or electroporation.

In some embodiments, the method further comprises isolating the recombinant lectin protein which has been expressed. This isolation step results in a crude recombinant lectin protein (such as a protein comprising the amino acid sequence of SEQ ID NO: 1) being obtained. Isolation may comprise a centrifugation step, for example where the host cell is centrifuged to obtain a cell pellet. Isolation may further comprise resuspension of the cell pellet in a buffer, suitable buffers for which will be known to the skilled person. The isolation step may comprise lysis of the resuspended cell pellet, for example by using a homogenizer to disrupt the cell membrane. Cell lysis is optionally carried out at a pressure of approximately 16000-20000 psi.

In some embodiments, the method further comprises purifying the crude recombinant lectin protein. Purification results in the production of a recombinant lectin protein isolate. Purification may be carried out by any suitable technique, such as centrifugation (e.g. ultracentrifugation), size exclusion chromatography, ion exchange chromatography, electrophoresis, affinity chromatography, filtration (e.g. diafiltration) and high performance liquid chromatography (HPLC), or a combination thereof.

Thus, in some embodiments, the method comprises:
a) optionally, cloning a recombinant lectin gene into an expression vector and inserting the expression vector into a host cell;
b) culturing the host cell in a suitable medium, wherein said culturing comprises a growth phase which is carried out at a temperature of from 25° C. to 40° C., and an expression phase during which the recombinant lectin protein encoded by the recombinant lectin gene is expressed, wherein the expression phase is carried out at a temperature of from 15° C. to 30° C. and wherein the carbon:nitrogen ratio is maintained during the expression phase at from 3:1 to 6:1;

c) optionally, isolating the recombinant lectin protein expressed in (b) to obtain a crude recombinant lectin protein; and d) optionally, purifying the crude recombinant lectin protein to obtain a recombinant lectin protein isolate.

In some embodiments, purifying the crude recombinant lectin protein comprises at least one chromatography step. In some embodiments, the at least one chromatography step comprises ion exchange chromatography and/or hydrophobic interaction chromatography.

In some embodiments, purifying the crude recombinant lectin protein comprises:

i) initial purification of the crude recombinant lectin protein by anion exchange chromatography to obtain a first purified elute;

ii) optional purification of the first purified elute by hydrophobic interaction chromatography to obtain a second purified elute;

iii) optional purification of the second purified elute by cation exchange chromatography to obtain a third purified elute;

iv) further purification of the second or third purified elute by anion exchange chromatography to obtain a fourth purified elute; and v) buffer exchange of the fourth purified elute by diafiltration to obtain a purified recombinant lectin protein isolate.

Advantageously, the purification steps described above enable recombinant lectin protein to be obtained in high purity (97-99% pure) without the need for chemical or enzymatic treatment.

In a second aspect of the invention, there is provided an expression construct comprising the nucleotide sequence of SEQ ID NO: 5.

In a third aspect of the invention, there is provided a host cell comprising the expression construct of the second aspect to the invention.

It will be understood that any of the embodiments described herein can be combined in any way and with any aspect of the invention, unless otherwise stated.

In some particular embodiments, the present invention relates to a process to prepare a recombinant lectin protein, such as a protein comprising the amino acid sequence of SEQ ID NO: 1, wherein the process comprises:

a. cloning of a nucleotide sequence (e.g. the sequence of SEQ ID NO:5), encoding the recombinant lectin protein into a recombinant host cell while embedded in a vector, to prepare a clone;

b. fed batch fermentation of the clone prepared in step 'a' for expression of the recombinant lectin protein (e.g. having amino acid sequence of SEQ ID NO:1) in a suitable medium at an initial temperature of about 25° C.-40° C. and induction phase temperature of about 15° C.-30° C., having a feeding rate such that the ratio of Carbon to Nitrogen source is 3:1 to 6:1 to obtain a fermentation product;

c. isolation and clarification of the fermentation product obtained in step 'b' to get a crude recombinant lectin protein (e.g. having amino acid sequence of SEQ ID NO:1); and d. purification of the crude recombinant lectin protein (e.g. having amino acid sequence of SEQ ID NO:1) obtained in step 'c'. Optionally, purification comprises the steps of:

i. initial purification of the crude recombinant lectin protein (e.g. having amino acid sequence of SEQ ID NO:1) by anion exchange chromatography to obtain first purified elute;

ii. optional purification of first purified elute obtained from step i by Hydrophobic interaction chromatography to obtain second purified elute;

iii. purification of second purified elute obtained from step ii or first purified elute obtained from step i, by cation exchange chromatography to obtain third purified elute;

iv. further purification of the third purified elute obtained in step iii or second purified elute obtained from step ii by anion exchange chromatography to obtain purified elute;

v. buffer exchange of purified elute obtained from step iv by diafiltration to obtain recombinant lectin protein (e.g. having amino acid sequence of SEQ ID NO:1) as pure product.

The present invention further relates to fed batch fermentation of recombinant bacterial cell in a suitable medium, wherein the feeding rate of carbon source during fermentation is 0.5 to 2 $gL^{-1} h^{-1}$ and that of nitrogen source is 0.4 to 1.5 $gL^{-1} h^{-1}$ to obtain the fermentation product.

The present invention further relates to a process of purification of crude recombinant lectin, such as the protein having amino acid sequence of SEQ ID NO: 1, wherein the process comprises:

a. initial purification of crude recombinant lectin protein (e.g. having amino acid sequence of SEQ ID NO:1) by anion exchange chromatography to obtain first purified elute;

b. optional purification of first purified elute obtained from step a by Hydrophobic interaction chromatography to obtain second purified elute;

c. purification of second purified elute obtained from step b or first purified elute obtained from step a, by cation exchange chromatography to obtain third purified elute;

d. further purification of the third purified elute obtained in step c or second purified elute obtained from step b by anion exchange chromatography to obtain purified elute;

e. buffer exchange of purified elute obtained from step d by diafiltration to obtain recombinant lectin protein (e.g. having amino acid sequence of SEQ ID NO:1) as pure product.

The present invention also relates to the clone used for production of recombinant lectin having amino acid sequence of SEQ ID NO:1 comprising nucleotide sequence of SEQ ID NO:5 encoding amino acid sequence of SEQ ID NO:1, in a recombinant host cell while embedded in a vector.

The present invention further relates to recombinant lectin having amino acid sequence of SEQ ID NO: 1, as prepared by the process disclosed herein.

Advantageously, in some embodiments the process of the present invention gives desired product in more than 90%, more than 95% or more than 97% yield.

The purity of the product recombinant lectin protein may be at least 90%, at least 95%, at least 97% or at least 99%, when measured using standard methods such as anion exchange chromatography.

The present invention relates to a process to prepare recombinant lectin having amino acid sequence of SEQ ID NO: 1, wherein the process comprises:

a. cloning of nucleotide sequence of SEQ ID NO: 5, encoding amino acid sequence of SEQ ID NO:1 in a recombinant host cell while embedded in a vector, to prepare a clone;
b. fed batch fermentation of the clone prepared in step 'a' for expression of recombinant lectin having amino acid sequence of SEQ ID NO:1, in a suitable medium at an initial temperature of about 25° C.-40° C. and induction phase temperature of about 15° C.-30° C., having a feeding rate such that the ratio of carbon to nitrogen source is 3:1 to 6:1 to obtain a fermentation product;
c. isolation and clarification of the fermentation product obtained in step 'b' to get crude recombinant lectin having amino acid sequence of SEQ ID NO:1; and
d. purification of the crude recombinant lectin having amino acid sequence of SEQ ID NO:1 obtained in step 'c', comprising the steps of:
  i. initial purification of crude recombinant lectin having amino acid sequence of SEQ ID NO:1 by anion exchange chromatography to obtain first purified elute;
  ii. optional purification of first purified elute obtained from step i by Hydrophobic interaction chromatography to obtain second purified elute;
  iii. purification of second purified elute obtained from step ii or first purified elute obtained from step i, by cation exchange chromatography to obtain third purified elute;
  iv. further purification of the third purified elute obtained in step iii or second purified elute obtained from step ii by anion exchange chromatography to obtain purified elute;
  v. buffer exchange of purified elute obtained from step iv by diafiltration to obtain recombinant lectin having amino acid sequence of SEQ ID NO:1 as pure product.

Cloning and expression of recombinant lectin having amino acid sequence of SEQ ID NO: 1

According to an aspect of the invention the host cell used for production of recombinant lectin having the amino acid sequence of SEQ ID NO: 1 may be a bacterial cell or yeast. The preferred bacterial cell is *E. coli*, particularly the strain, *E coli* BL21 DE3 Gold. The nucleotide sequence of SEQ ID NO:5 coding for the recombinant lectin with amino acid sequence of SEQ ID NO:5 may be cloned in a vector preferably pET27b. The plasmid may then be transformed and expressed in hosts *E coli* BL21 DE3 Gold.

Fermentation Process

In an exemplary embodiment, *E. coli* BL21 DE3 Gold strains containing plasmid pET27b containing a nucleotide sequence encoding a recombinant lectin protein are grown in an inoculum medium containing Luria HiVeg broth (20 g/l), $Na_2HPO_4$ (7.5 g/l), Dextrose (5 g/l), $MgSO_4.7H_2O$ (1 g/l), kanamycin to a final concentration of 20 µg/ml and 0.1% (v/v) trace metal solution of $FeSO_4$, $ZnSO_4$, $CoCl_2$, $NaMoO_4$, $CaCl_2$, $MnCl_2$, $CuSO_4$ or $H_3BO_3$ in Hydrochloric acid. The inoculum is prepared by growing the cells at 30-40° C. for 12-16 hrs. Fed batch fermentation of recombinant *E. coli* BL21 DE3 Gold strains may be carried out in a production medium comprising yeast extract (10 g/l), Dextrose (12 g/l), $KH_2PO_4$ (3 g/l), $K_2HPO_4$ (12.5 g/l), $(NH_4)_2SO_4$ (5 g/l), NaCl (0.5 g/l), $MgSO_4.7H_2O$ (1 g/l) and 0.1% (v/v) trace metal solution of $FeSO_4$, $ZnSO_4$, $CoCl_2$, $NaMoO_4$, $CaCl_2$, $MnCl_2$, $CuSO_4$ or $H_3BO_3$ in Hydrochloric acid. Kanamycin may be added to a final concentration of 20 µg/ml. Feeding may be initiated with a suitable carbon source such as glucose or glycerol, preferably 50% (w/v) of glycerol, and nitrogen source such as tryptone, peptone or yeast extract, preferably 40% (w/v) of yeast extract. Feeding may be initiated after log 5 hours at predetermined feeding rates. Feeding rate of the carbon source during fermentation may be 0.5 to 2 $gmL^{-1} h^{-1}$ and that of the nitrogen source may be 0.4 to 1.5 $gmL^{-1} h^{-1}$, maintaining a C:N ratio in the range of 3:1 to 6:1, preferably with the C:N ratio of 4:1. Those skilled in the art may vary the rates and the amounts as per their suitability, since they are specific for the parameters demonstrated for the particular batch sizes.

The initial growth phase may be carried out at 25° C. to 40° C., and at 15° C. to 30° C. during induction phase followed by purification by a sequence of column chromatography. The temperature may be maintained during initial growth at about 25° C.-40° C. preferably about 37° C. The temperature may be reduced for the induction phase and maintained at about 15° C.-30° C. preferably about 22° C.

The initial growth of the culture may be carried out with about 1-2 vvm aeration, dissolved oxygen maintained at 50%-60% and pH maintained at 6.6-7.2 with alkali such as sodium hydroxide. The total culture time may be from 20 to 50 hours or from 30 to 40 hours, preferably about 36 hrs. Feeding of carbon and nitrogen source may be continued until the end of the culture run time.

Expression of a recombinant lectin protein (e.g. having amino acid sequence of SEQ ID NO:1) may be carried out by inducing a host cell (such as *E. coli*) culture broth with an inducer such as lactose or isopropyl thio-galacto-pyranoside (IPTG), preferably IPTG at a concentration of about 50 µM to 1500 µM, preferably about 1000 µM. The culture may be induced at the cell density measuring at least about 20-50, preferably about 30-50 at about 600 nm.

Expression of the recombinant lectin protein can be demonstrated by SDS-PAGE analysis of the total cell lysate and lysis supernatant. Recombinant protein expression may be about 50% to 60% of total protein and expressed in soluble form in the cytoplasm. The yield of recombinant lectin protein may be at least about 5-9 g/L of fermentation broth as analyzed by SDS-PAGE.

Isolation of soluble recombinant lectin protein may be carried out by harvesting cells by centrifugation to obtain the cell pellet, and re-suspending the cells in a suitable buffer, which may be pre-chilled to a temperature of about 6° C.-10° C. Cell disruption may be carried out on a homogenizer (MiniDebee), optionally under high pressure of about 16000-20000 psi. The cell lysate thus obtained can be processed further for purification of soluble recombinant lectin protein, for example by using different chromatographic steps.

Purification of Recombinant Lectin Protein

A process for the purification of recombinant lectin protein obtained from the cell lysate obtained from the fermentation process may comprise the steps of:
a Column 1: Anion exchange chromatography
b Column 2: Hydrophobic interaction chromatography
c Column 3: Cation exchange chromatography
d Column 4: Anion exchange chromatography In some embodiments, the total cell lysate obtained after cell lysis is clarified using about 0.1 µm tangential flow filtration system to obtain a clear solution.

In some embodiments the clarified cell lysate is subjected to anion exchange column chromatography using resins such as Cellufine Max Q-r, Source 30Q, Source 15Q and DEAE Sepharose. The column may be equilibrated with suitable buffer, for example buffer having about 10-30 mM Tris, about 0.5-2 mM EDTA and a pH of about 7.5-9.0. After loading, the column may be washed with a buffer having conductivity in the range of about 4 to 8 mS/cm. Elution may be performed with a buffer containing about 10-30 mM Tris, about 0.5-2 mM EDTA and Sodium chloride with conductivity of about 15-20 mS/cm.

In some embodiments the protein obtained from anion exchange column is optionally subjected to Hydrophobic Interaction column Chromatography. The resins used may be Cellufine Max Butyl, Butyl Sepharose, Phenyl Sepharose etc. The column may be equilibrated with about 20-30 mM Sodium acetate buffer containing about 0.5-2 M ammonium sulphate, about 0.5-2 mM EDTA with pH about 4 to 5. Elution may be performed with about 20-30 mM Sodium acetate buffer having about 0.5-2 mM EDTA, about 10-20 g/L ammonium sulphate, pH in the range of about 4 to 5 and conductivity in the range of about 2 to 100 ms/cm. The elute obtained after Hydrophobic Interaction column Chromatography or from the anion exchange column may then be subjected to cation exchange column chromatography using resins such as SP Sepharose, CM Sepharose, Cellufine Max S-h etc. The column may be equilibrated with about 20-30 mM Sodium acetate buffer containing about 0.5-2.0 mM EDTA and pH in the range of about 4 to 5. The elution buffer may contain about 20-30 mM Sodium acetate, about 0.5-2 mM EDTA, about 0.3-1 M Sodium chloride and pH in the range of about 4 to 5. Prior to elution, a step gradient in the range of about 15-25% may be given. Elution may be done with a step gradient in the range of about 50-80%.

In some embodiments, elute obtained in the cation exchange chromatography is diluted with water for injection (WFI) or Purified water (PW) in about 1:2 to 1:5 ratio. The pH of the protein solution may then be adjusted to about 7.5 to 8.5 with sodium hydroxide, tris buffer or glycine buffer pH 11.0 followed by buffer exchange with Tris buffer, pH 7.5-8.5 using tangential flow filtration system till the conductivity decreases in the range of about 1-5 mS/cm. The protein solution may then be subjected to anion exchange column chromatography. Resins such as Cellufine Max Q-r, Source Q15, Source Q30 or DEAE Sepharose can be used. The column may be equilibrated with about 20-30 mM Tris buffer with pH in the range of about 7.5 to 8.5. The elution may be performed with buffer containing about 20-30 mM Tris, about 0.3-1 M Sodium chloride and pH in the range of about 7.5 to 8.5. For elution, a linear gradient up to about 15%, for 3-20 column volumes may be given. The elute thus obtained may be buffer exchanged with suitable buffer such as Tris buffered saline, phosphate buffered saline, acetate buffer by diafiltration using 3, 5 or 10 KDa cutoff membrane.

The buffer exchanged protein can be stored at about 2-8° C. to maintain biological activity. Alternatively, elute obtained after second anion exchange chromatography can be buffer exchanged against water for injection and subsequently lyophilized to obtain powder form of protein.

The purity of the recombinant lectin protein can be checked by anion exchange high performance liquid chromatography. A recombinant lectin protein having the amino acid sequence of SEQ ID NO:1 thus obtained after a series of chromatographic separation has been found to be 97%-99% pure. The percentage of recombinant lectin protein having amino acid sequence of SEQ ID NO:1 with unprocessed initiator methionine was found to be about 10-15% (relative abundance with respect to Met-free lectin).

The present invention thus provides a method of expressing a recombinant lectin protein, such as that of SEQ ID NO: 1, in a vector, that has tight regulation over expression of protein, and its soluble expression in host cells. The process of the invention is controllable and scalable, and overcomes the disadvantages of the previous processes. The present invention thus describes an industrially scalable process to produce gram quantities of recombinant lectin.

Thus the main object of the invention, to overcome disadvantages of prior references and device highly efficient process to prepare amino acid sequence of SEQ ID NO:1 is achieved.

The yield of recombinant lectin having amino acid sequence of SEQ ID NO:1 may be 1.5-3.0 g/L of fermentation broth. Thus another object of the invention that is to provide a process which is high yielding and cost effective and which can be performed using easily available raw material is also achieved. The present process is cost effective as the raw materials required to prepare high amounts of recombinant lectin having amino acid sequence of SEQ ID NO:1 is considerably low. Also the process does not require very high or low temperatures or costly instruments to perform. Therefore the process becomes cost effective and easily scaleable.

The present invention further relates to fed batch fermentation of recombinant bacterial cell in a suitable medium, wherein the feeding rate of carbon source during fermentation is about 0.5 to 2 $gL^{-1} h^{-1}$ and of nitrogen source is about 0.4 to 1.5 $gL^{-1} h^{-1}$ to obtain the fermentation product.

The initial fermentation/growth phase may be carried out at about 25° C. to 40° C. and then the temperature is reduced to about 15° C. to 30° C. during induction phase followed by purification by a sequence of column chromatography.

In some embodiments, the initial growth of the culture was carried out with about 1-2 vvm aeration, dissolved oxygen maintained at about 50-60% and pH maintained at about 6.6-7.2 with alkali such as sodium hydroxide. In some embodiments, the temperature maintained during initial growth was about 25° C.-40° C. During induction phase the temperature may be reduced and maintained at about 15° C.-30° C. Fermentation runtime may be at least about 20-50 hrs. Feeding of carbon and nitrogen source may be continued till the end of fermentation run time.

In some embodiments clarified cell lysate is subjected to anion exchange column chromatography using resins such as Cellufine Max Q-r, Source 30Q, Source 15Q and DEAE Sepharose. A column may be equilibrated with buffer having about 10-30 mM Tris buffer, about 0.5-2 mM EDTA and pH about 7.5-9.0. After loading, the column may be washed with buffer having conductivity in the range of about 4 to 8 mS/cm. Elution may be performed with buffer containing 10-30 mM Tris, 0.5-2 mM EDTA and Sodium chloride with conductivity of 15-20 mS/cm.

In some embodiments the protein obtained from anion exchange column is optionally subjected to Hydrophobic Interaction column Chromatography. The resins used may be Cellufine Max Butyl, Butyl Sepharose, Phenyl Sepharose etc. A column may be equilibrated with 20-30 mM Sodium acetate buffer containing about 0.5-2 M ammonium sulphate, about 0.5-2 mM EDTA with pH about 4.0 to 5.0. Elution may be performed with about 20-30 mM Sodium acetate buffer having about 0.5-2 mM EDTA, about 10-20 g/L ammonium sulphate, pH in the range of about 4 to 5 and conductivity in the range of about 2 to 100 ms/cm. Elute obtained after Hydrophobic Interaction column Chromatography or from anion exchange column may then be subjected to cation exchange column chromatography using resins such as SP Sepharose, CM Sepharose, Cellufine Max S-h etc. A column may be equilibrated with about 20-30 mM Sodium acetate buffer containing about 0.5-2.0 mM EDTA and pH in the range of about 4 to 5. The elution buffer may contain about 20-30 mM Sodium acetate, about 0.5-2 mM EDTA, about 0.3-1 M Sodium chloride and pH in the range of about 4 to 5. Prior to elution, a step gradient in the range of about 15-25% may be given. Elution may be done with a step gradient in the range of about 50-80%.

The elute obtained in cation exchange chromatography may be diluted with WFI or PW in about 1:2 to 1:5 ratio. pH of the protein solution may then be adjusted to about 8 with NaOH, tris buffer or glycine buffer pH 11.0. This may be followed by buffer exchange with Tris buffer, pH 7.5-8.5 using tangential flow filtration system till the conductivity decreases in the range of about 1-5 mS/cm. The protein solution may then be subjected to anion exchange column chromatography. Resins such as Cellufine Max Q-r, Source Q15, source Q30 or DEAE Sepharose can be used. The column may be equilibrated with about 20-30 mM Tris buffer having pH in the range of about 7.5 to 8.5. The elution may be performed with buffer containing about 20-30 mM Tris, about 0.3-1 M Sodium chloride and pH in the range of about 7.5 to 8.5. For elution, a linear gradient up to about 15%, for 3-20 column volumes may be given. The elute thus obtained may be buffer exchanged with suitable buffer such as Tris buffered saline, phosphate buffered saline, acetate buffer by diafiltration using 3, 5 or 10 KDa cutoff membrane. The buffer exchanged protein can be stored at 2-8° C. to maintain biological activity. Alternatively, elute obtained after second anion exchange chromatography can be buffer exchanged against water for injection and subsequently lyophilized to obtain powder form of protein. The purity of the recombinant lectin having amino acid sequence of SEQ ID NO:1 may be checked by anion exchange high performance liquid chromatography. Recombinant lectin having amino acid sequence of SEQ ID NO:1 thus obtained after this series of chromatographic separation is 97%-99% pure. The percentage of recombinant lectin having amino acid sequence of SEQ ID NO:1 with un-processed initiator methionine was 10-15% (relative abundance with respect to Met-free lectin).

The present invention relates to the clone used for production of recombinant lectin having amino acid sequence of SEQ ID NO:1 comprising nucleotide sequence of SEQ ID NO:5 encoding amino acid sequence of SEQ ID NO:1, in a recombinant host cell while embedded in a vector.

EXAMPLES

The examples are given to demonstrate the best mode of performing the invention and do not restrict the scope of the invention in any manner.

Example 1: Cloning of Lectin SEQ ID NO: 5 in pET27b Vector and Expression in *E. coli* BL21 DE3

The nucleotide sequence (SEQ ID NO:5) coding for the recombinant lectin having amino acid sequence of SEQ ID NO:1 previously cloned in pET20b vector (as disclosed in patent number WO 2010/095143 A2) was sub-cloned into pET27b vector. *E. coli* BL21 DE3 cells harboring SEQ ID NO:5 cloned in pET20b were grown in Luria Hiveg broth (Himedia, Mumbai, India). Plasmid was isolated from the cells using GeneJET plasmid miniprep kit (Thermo Scientific) as per manufacturer's instructions. Plasmid pET20b was digested with restriction enzymes NdeI and BamHI (New England Biolabs). The digested plasmid was run on agarose gel electrophoresis and released insert was eluted from gel using GeneJET gel extraction kit (Thermo Scientific). Similarly vector pET27b was isolated and digested with same restriction enzymes (NdeI and BamHI). The insert released from pET20b (SEQ ID NO:5) was cloned into pET27b vector (pET27b-Lec) and transformed into *E. coli* BL21 DE3 (Gold). Clones were screened by colony PCR and positive clone was further used for expression analysis. The positive clone was grown in Hiveg Luria broth at 37° C., induced with 0.25 mM IPTG at 1-1.2 cell density (OD600 nm) and further grown for 4 hours. The expression of recombinant lectin having amino acid sequence of SEQ ID NO:1 was confirmed by SDS-PAGE analysis. The sequence of the insert in vector pET27b was confirmed by DNA sequencing of the isolated plasmid. Glycerol stocks of positive clone were prepared and maintained at −80° C.

Example 2: Fermentation Process

Culture from glycerol stock was inoculated into medium containing 2% Hiveg Luria broth, 0.75% $Na_2HPO_4$, 0.5% dextrose and kanamycin (20 µg/ml). The culture was grown at 30±2° C. and 110 rpm for 16 hours. Approximately 300 ml culture was inoculated into 2.3 L of production medium containing. 1% yeast extract (w/v), 1.2% Dextrose (w/v), 0.3% $KH_2PO_4$ (w/v), 1.25% $K_2HPO_4$ (w/v), 0.5% $(NH_4)_2SO_4$ (w/v), 0.05% NaCl (w/v), 0.1% $MgSO_4.7H_2O$ (w/v), 0.1% (v/v) trace metal solution, kanamycin (20µ/ml). Fermentation was carried out in 5 L fermenter (BIOSTAT B, Sartorius Stedim) with 1-2 vvm aeration, dissolved oxygen was maintained at 50-60% and pH maintained was maintained at 6.6-7.0 with alkali. Initial growth was carried out at a temperature of 37° C. Temperature was gradually decreased and maintained at 22° C. during the induction phase. Feeding of carbon (glycerol) and nitrogen source (yeast extract) was initiated after 5 log hrs at predetermined feeding rates, maintaining C:N ratio in the range of 4:1. Culture was induced at cell density of ~45 ($OD_{600}$) with 1 mM IPTG. Fermentation was continued till 24 hrs and culture broth was harvested by centrifugation at 9000 rpm for 15 minutes. The wet weight of cell mass obtained from fermentation broth was 372 g.

Example 3: Isolation of Recombinant Lectin Having Amino Acid Sequence of SEQ ID NO:1 from Cells Cell pellet was suspended in lysis buffer (25 mM tris, 1 mM EDTA, pH 8.5) in a ratio of 1:10 (w/v) and stirred for at least 2 hr on an overhead stirrer to form a homogenous suspension. The suspension was lysed by high pressure homogenization at 18,000 psi. The cell lysate was centrifuged at 9,000 rpm for 15 min at 15° C. The resultant supernatant was retained and processed further for purification of recombinant lectin having amino acid sequence of SEQ ID NO:1.

Example 4: Removal of Nucleic Acid Impurities and Clarification of the Protein Solution by Microfiltration Supernatant was treated with at least 0.025% polyethyleimine by stirring for 15-30 mins. The total cell lysate obtained after Polyethyleneimine treatment was clarified using a 0.1 µm hollow fiber of 3600 cm² area pre equilibrated with 25 mM Tris buffer containing 1 mM EDTA, pH 8.0±0.5. Transmembrane pressure of 5-10 psi was maintained throughout the clarification process. The retentate was diafiltered in step mode with the equilibration buffer mentioned above to recover the recombinant lectin having amino acid sequence of SEQ ID NO:1 in permeate. Recovery of above 90% was obtained in permeate for recombinant lectin having amino acid sequence of SEQ ID NO:1. Total protein of 84.4 g as measured by Optical density at 280 nm was recovered in permeate. Purity of the protein of interest was 49.4% as measured by HPLC.

Example 5: Protein Purification by Ion Exchange Chromatography (Column 1)

The clarified protein solution was loaded onto Cellufine Max Q-r resin pre equilibrated with 25 mM Tris buffer containing 1 mM EDTA, pH 8.0±0.5. Post loading, equilibration buffer wash was given followed by washing with the equilibration buffer containing 1-3 g/L NaCl. Protein was eluted with 25 mM Tris buffer containing 1 mM EDTA, 11-15 g/L NaCl, pH 8±0.5. Total Protein recovered at this column was 41.6 g of 77.4% purity of the active protein.

Example 6: Protein Precipitation and Purification by Hydrophobic Interaction Chromatography (HIC—Column 2)

The pH of the column 1 elute was adjusted to 4.5 with acetic acid followed by ammonium sulphate precipitation. The solution was then centrifuged and the clear supernatant was processed on the HIC resin (Cellufine Max Butyl) for further purification. Column was equilibrated with 25 mM sodium acetate buffer containing 1 mM EDTA, 0.5-2M ammonium sulphate, pH 4.5 followed by loading the protein solution. Post loading, equilibration buffer wash was given followed by elution with elution buffer containing 25 mM Sodium acetate, 1 mM EDTA, 15 g/L ammonium sulphate, pH 4.5. Total Protein of 27.5 g was eluted from column 2 having a purity of 90.3%.

Example 7: Protein Purification by Cation Exchange Chromatography (Column 3)

The protein obtained from column 2 was diluted to approximately 20 mS/cm conductivity with purified water, and loaded onto SP Sepharose FF resin pre equilibrated with 25 mM Sodium acetate buffer containing 1 mM EDTA, pH 4.5. Post loading, equilibration buffer wash was given to the column, followed by a step gradient of 20% Elution buffer containing 25 mM Sodium acetate, 1 mM EDTA, 0.5 M NaCl, pH 4.5. Elution was carried out by giving a step gradient of 50-70% Elution buffer. Total of 24.6 g protein having a purity of 93.0% was recovered from the column. Buffer exchange of the column 3 elute was carried out on 3 KDa membrane to get the protein in 25 mM Tris buffer, pH 8.0.

Example 8: Protein Purification by Anion Exchange Chromatography

After buffer exchange, 20.9 g protein was obtained and processed onto Source 30Q resin. The column was equilibrated with 25 mM Tris buffer, pH 8.0 followed by loading of the protein solution. Post loading, column was washed with the equilibration buffer. Elution was then carried out by giving a linear gradient of the elution buffer containing 25 mM Tris, 0.5 M NaCl, pH 8.0, 15 column volumes. Single peak was obtained which when analyzed by HPLC showed a purity of >99.0%. Total of 9.0 grams was obtained as measured by optical density at 280 nm considering 1OD at 280 nm equals 1 mg. The final elute was buffer exchanged against TBS Buffer (50 mM Tris buffer, 150 mM NaCl, pH 7.8).

Example 9: Physico-Chemical Characterization of Recombinant Lectin Having Amino Acid Sequence of SEQ ID 1

The purity of recombinant lectin having amino acid sequence of SEQ ID NO:1 was determined by SDS-PAGE and HPLC analysis. The purity of recombinant lectin having amino acid sequence of SEQ ID NO:1 by HPLC analysis was 97-99%. SDS-PAGE analysis of recombinant lectin having amino acid sequence of SEQ ID NO:1 showed single band at molecular weight of ~16 KDa. The identity of the protein was confirmed by western blotting and biological activity was confirmed by Haemagglutination assay and in vitro cell based assays using various cancer cell lines. The molecular mass of the purified lectin recombinant lectin having amino acid sequence of SEQ ID NO: 1 was 16044 Dalton.

Example 10: Fermentation Process Conditions

Culture from glycerol stock in accordance with the previous examples was inoculated into medium containing 2% Hiveg Luria broth, 0.75% $Na_2HPO_4$, 0.5% dextrose and kanamycin (20 μg/ml). The culture was grown at 37° C. and 110 rpm for 16 hours for batches 1-3.

For batches 4 and 5, culture from glycerol stock in accordance with the previous examples was inoculated into medium as above, except that the culture was grown at 30° C. and 110 rpm for 19 hours.

Approximately 300 ml culture was then inoculated into 2.3 L of production medium.

The production medium was as described in Example 2 except for the following differences in each batch (and as shown in Table 1):

TABLE 1

Analysis of proportion of methionine lectin obtained from different fermentation conditions.

| Batch No. | Change implemented | Induction OD | Final OD | Batch run time (h) | Feed rate Total glycerol added (g/L) | Remark |
|---|---|---|---|---|---|---|
| Batch 1 | Production medium contained dextrose (12 g/L). Batch started at 37° C. and temperature decreased gradually to 22° C. by log $4^{th}$ hour. Induction with 1 mM IPTG | 54 | 199 | 25 | 102 | Met-lectin >50% |
| Batch 2 | Production medium contained dextrose (12 g/L). Batch started at 37° C. and temperature decreased gradually to 22° C. by log $4^{th}$ hour. Induction with 1 mM IPTG | 44 | 176 | 25 | 75 | Met-lectin 26% |

TABLE 1-continued

Analysis of proportion of methionine lectin obtained from different fermentation conditions.

| Batch No. | Change implemented | Induction OD | Final OD | Batch run time (h) | Feed rate Total glycerol added (g/L) | Remark |
|---|---|---|---|---|---|---|
| Batch 3 | Batch started at 37° C. and temperature reduced to 18° C. by 5th hour | 40 | 128 | 25 | 70 | Met-lectin 16% |
| Batch 4 | Batch started at 30° C. and temperature reduced to 18° C. by 6th hour. Inoculum was grown at 30° C. for 19 hrs. Induction with 0.25 mM IPTG | 27 | 97.8 | 33 | 35 | Met-lectin 13% |
| Batch 5 | Batch started at 30° C. and temperature reduced to 18° C. by 6th hour. Inoculum was grown at 30° C. for 19 hrs. Induction with 0.25 mM IPTG | 30 | 117 | 48 | 40 | Met-Lectin 12% |

Batches 1-3: Production medium contained 12 g/L of dextrose in accordance with Example 2. Batches 4-5: Production medium contained 10 g/L of dextrose instead of 1.2% dextrose as described in Example 2.

For each batch, fermentation was carried out in a 5 L fermenter (BIOSTAT B, Sartorius Stedim) with 1-2 vvm aeration, dissolved oxygen was maintained at 50-60% and pH maintained was maintained at 6.6-7.0 with alkali.

The temperature of the production medium was initially kept at 37° C., with the following conditions:

Batches 1-2—The temperature was gradually decreased to 22° C. by log $4^{th}$ hour. This temperature was maintained in the induction phase, which was initiated with 1 mM IPTG. The total batch run time was 25 hours.

Feeding of carbon (glycerol) and nitrogen source (yeast extract) was initiated after 4 log hrs. The total amount of glycerol fed to batch 1 was 102 g/L and to batch 2 was 75 g/L.

Batch 3—The temperature was gradually decreased to 18° C. by the $5^{th}$ hour. This temperature was maintained in the induction phase, which was initiated with 1 mM IPTG. The total batch run time was 25 hours.

The total amount of glycerol fed to batch 3 in the induction phase was 70 g/L.

For batches 1-3, inducer was added 4-6 hours post inoculation into the production medium. The addition of inducer initiated the induction (expression) phase.

Batches 4-5—After inoculation into the production medium the temperature was gradually decreased to 18° C. by the $6^{th}$ hour. This temperature was maintained in the induction (expression) phase, which was initiated with 0.25 mM IPTG at nine hours post inoculation. The total batch run time was either 33 (batch 8) or 48 (batch 9) hours.

The total amount of glycerol fed to batch 4 in the induction phase was 35 g/L, while the total amount of glycerol fed to batch 5 in the induction phase was 40 g/L.

Culture broth was harvested by centrifugation at 9000 rpm for 15 minutes and the recombinant lectin isolated and purified in accordance with the invention. The proportion of methionine lectin in the isolated lectin was then analysed.

Over 50% of the lectin isolated in batches 1 was methionine-lectin. This was reduced to 26% in batch 2, 16% in batch 3, 13% in batch 4 and 12% in batch 5.

Example 11: Doubling Time

The doubling time of *E. coli* was determined at different time points and temperatures in a sample fermentation process, i.e. post inoculation into a production medium. The results are shown in Table 2. For this example, inducer, in this embodiment IPTG was added 9 hours post inoculation.

Thus, for this example the growth phase will be understood to be the time points prior to 9 hours, and the expression phase will be understood to be the time points at and following the addition of inducer.

TABLE 2

Doubling time of *E. coli* at different fermentation conditions

| Temperature and Log hr | Doubling time (minute) |
|---|---|
| 30° C. (Log 0 to log 1 hr)* | 85 |
| 30° C. (Log 0.5 to log 1 hr)§ | 42 |
| 30° C. to 25° C. (Log 0 to 3 hr)£ | 100 |
| 18° C. Before induction (log 7 to log 9 Hr) | 103 |
| 18° C. after induction (Log 9 hr onwards) | 145 |
| 18° C. Average (log 7 to log 11 Hr) | 120 |

*Includes initial lag phase and exponential phase;
§Exponential phase;
£Average of log 0 to 3 hours

Example 12: Purification of Recombinant Lectin

In this example, recombinant lectin is isolated and purified from a culture broth such as that produced in Example 10.

The culture broth is centrifuged at 9000 rpm for 15 minutes at 15° C. The pellet obtained is resuspended in lysis buffer (25 mM tris, 1 mM EDTA, pH 8.0). The cells are lysed by high pressure homogenisation at 18000 psi. The lysate is clarified using 0.1 micron hollow fiber pre-equilibrated with lysis buffer. The clarified protein solution is subjected to a series of chromatographic steps to purify the recombinant lectin.

Anion exchange chromatography: The clarified protein solution is loaded on Cellufine Max Q-r column equilibrated with 25 mM Tris, 1 mM EDTA, and pH 8.0 at 60-80 mg/ml binding strength. After loading, the column is washed with 2-3 column volumes of the equilibration buffer. Further, the column is washed with equilibration buffer containing sodium chloride having conductivity of ~5 mS/cm. Elution of the bound protein is done with 25 mM Tris buffer, 1 mM EDTA, pH 8.0 containing sodium chloride having conductivity of 18-20 mS/cm. The entire peak is collected as a single fraction which contains the protein of interest along with a few other impurities.

Cation exchange chromatography: The eluate from the anion exchange chromatography is subjected to cation exchange chromatography using SP Sepharose FF column. The pH of the eluate is adjusted to 4.5 with acetic acid. The protein is then loaded onto SP Sepharose FF column equilibrated with 25 mM sodium acetate buffer containing 1 mM EDTA, pH 4.5 (Buffer A) at 40-50 mg/ml binding on the resin. After loading, the column is washed with 2-3 column volumes of the equilibration buffer. The column is then washed in step gradient with 20% buffer B (Buffer B: Buffer A+0.5M NaCl). Elution is carried out with a step gradient of 70% buffer B. The eluate is then immediately diluted in 1:1 ratio with water to prevent aggregation of protein. The eluted protein is buffer exchanged with 25 mM Tris buffer, pH 8.0 using 3 KDa membrane. Anion exchange chromatography: After the buffer exchange protein is loaded on Source 30Q resin, a column is equilibrated with 25 mM Tris buffer, pH 8.0 followed by loading of the protein solution. Post-loading, the column is washed with the equilibration buffer. Elution is then carried out by giving a linear gradient of the elution buffer containing 25 mM Tris, 0.5 M NaCl, pH 8.0, 15 column volumes. The final eluate is then buffer exchanged against TBS Buffer (50 mM Tris buffer, 150 mM NaCl, pH 7.8). The eluted protein is analysed by HPLC for purity and concentration.

---

Summary of Sequences

SEQ ID NO. 1:
TYKITVRVYQTNPDAFFHPVEKTVWKYANGGTWTITDDQHVLTMGGSGTS
GTLRFHADNGESFTATFGVHNYKRWCDIVTNLAADETGMVINQQYYSQKN
REEARERQLSNYQVKNAKGRNFQIVYTEAEGNDLHANLIIG

SEQ ID NO. 2:
TYKITVRVYQTNPNAFFHPVEKTVWKYANGGTWTITDDQHVLTMGGSGTS
GTLRFHADNGESFTATFGVHNYKRWCDIVTNLAADETGMVINQQYYSQKN
REEARERQLSNYEVKNAKGRNFEIVYTEAEGNDLHANLIIG

SEQ ID NO. 3:
VYKITVRVYQTNPDAFFHPVEKTVWKYANGGTWSITDDQHVLTMGGSGTS
GTLRFHADNGESFTATFGVHNYKRWCDIVTNLAADETGMVINQQYYSQKN
REEARERQLSNYQVKNAKGRNFQIVYTEAEGNDLHANLIIG

SEQ ID NO. 4:
VYKITVRVYQTNPDAFFHPVEKTVWKYADGGTWSITDDQHVLTMGGSGTS
GTLRFHADNGESFTATFGVHDYKRWCDIVTDLAADETGMVINQEYYSEKD
REEARERQNSNYEVKDAKGRNFEIVYTEAEGNDLHADLIIG

SEQ ID NO: 5:
ATGACCTATAAAATTACCGTGCGCGTGTATCAGACCAACCCGGATGCCTT
TTTCCATCCGGTGGAAAAAACCGTGTGGAAATATGCGAATGGCGGTACCT
GGACGATTACGGATGATCAGCATGTGCTGACGATGGGTGGTAGCGGTACC
AGCGGCACCCTGCGTTTTCACGCAGATAATGGCGAAAGCTTCACCGCCAC
CTTTGGTGTGCATAATTATAAACGCTGGTGTGATATTGTGACCAACCTGG
CAGCGGATGAAACCGGCATGGTTATTAATCAGCAGTATTATAGTCAGAAA
AACCGCGAAGAAGCGCGTGAACGCCAGCTGAGTAACTATCAGGTGAAAAA
TGCGAAAGGCCGTAACTTCCAGATTGTTTATACCGAAGCGGAAGGCAATG
ATCTGCATGCGAACCTGATTATCGGC

---

The aspect of the present invention are:

1. A method of preparing a recombinant lectin protein, the method comprising:
expressing a recombinant lectin protein encoded by a recombinant lectin gene in a host cell in culture, wherein expression is performed under conditions for the cell such that the cell has a doubling time of no more than 160 minutes.

2. The method according to 1, wherein expression is performed under conditions for the cell such that the cell has a doubling time of at least 100 minutes.

3. The method according to 1 or 2, wherein expression is performed at a temperature of no more than 22° C.

4. The method according to any one of 1 to 3, wherein expression is performed at a temperature of at least 15° C.

5. The method according to any one of 1 to 4, wherein the method comprises culturing the host cell, said culturing comprising:
a growth phase during which the host cells are grown prior to protein expression; and
an expression phase during which protein expression is performed, wherein the growth phase is carried out at a temperature which is greater than the temperature at which the expression phase is performed.

6. The method according to 5, wherein the growth phase is carried out at a temperature of at least 25° C. and no more than 40° C.

7. The method according to 5 or 6, wherein the temperature is reduced from the growth phase to the expression phase over a period of at least 4 and no more than 7 hours.

8. The method according to any one of 1 to 7, wherein expression of the recombinant lectin protein is initiated by addition of an inducer to the culture.

9. The method of 8, wherein the inducer is added to the culture at a concentration of at least 0.1 mM and no more than 0.5 mM.

10. The method according to 8 or 9, wherein the inducer comprises IPTG.

11. The method according to any one of 1 to 10, wherein expression is carried out for at least 10 hours.

12. The method according to any one of 1 to 11, wherein a carbon source is added to the culture at a rate of no more than 2 $gL^{-1}$ $h^{-1}$ and/or a nitrogen source is added to the culture at a rate of no more than 1.5 $gL^{-1}$ $h^{-1}$ during expression.

13. The method of 12, wherein the carbon source is added to the culture at a rate of at least 0.5 $gL^{-1}$ $h^{-1}$.

14. The method of 12 or 13, wherein the nitrogen source is added to the culture at a rate of at least 0.4 $gL^{-1}$ $h^{-1}$.

15. The method according to any one of 12 to 14, wherein the carbon source comprises or consists of glycerol.

16. The method according to any one of 1 to 15, wherein the recombinant lectin protein comprises an amino acid sequence selected from
i) SEQ ID NO:1;
ii) SEQ ID NO:3;
iii) SEQ ID NO:4; or
iv) an amino acid sequence having at least 60% homology with i), ii) or iii).

17. The method according to 16, wherein the amino acid sequence of iv) is an amino acid sequence having at least 70%, 80%, 90%, 95% or 99% homology to i), ii) or iii).

18. The method according to any one of 1 to 17, wherein the method further comprises a step of isolating a crude recombinant lectin protein after the step of expressing the recombinant lectin protein.

19. The method according to 18, wherein the method further comprises purifying the crude recombinant lectin protein.

20. The method according to 19, wherein purifying the crude protein comprises at least one chromatography step.

21. The method according to 20, wherein the at least one chromatography step comprises anion exchange chromatography and/or cation exchange chromatography.

22. The method according to 20 or 21, wherein the at least one chromatography step comprises hydrophobic interaction chromatography.

23. The method according to any one of 19 to 22, wherein purifying the crude recombinant lectin protein comprises a filtration step.

24. The method according to any one of 1 to 23, wherein the host cell is *Escherichia coli*.

25. The method according to any one of 1 to 24, wherein the host cell comprises an expression construct comprising the recombinant lectin gene.

26. The method according to any one of 1 to 25, wherein the host cell culture has a volume of at least 10 L.

27. The method according to 26, wherein expression is carried out in an industrial fermenter.

---

We claim:

1. A method of preparing a recombinant lectin protein with improved cleavage of the initiator methionine, the method comprising expressing a recombinant lectin protein encoded by a recombinant lectin gene in a host cell in culture, wherein
   a. an induction phase is initiated by adding an inducer to the culture;
   b. the host cell is a recombinant *E. coli* cell, and expression during the induction phase is performed under conditions that cause the host cell to have a doubling time between 100 minutes and 160 minutes, wherein said conditions include the following:
   c. the induction phase is carried out at a temperature of at least 15° C. and no more than 22° C., and carbon to nitrogen ratio is maintained during the expression phase from 3:1 to 6:1; wherein the recombinant lectin protein is selected from
      i. SEQ ID NO:1;
      ii. SEQ ID NO:3;
      iii. SEQ ID NO:4; or
      iv. an amino acid sequence having at least 90%, 95%, 97%, 98%, or 99% homology with i, ii, or iii;
   d. the induction phase is carried out for at least 10 hours and the optical density of the culture is at least 25 and no more than 40;
   e. carbon source is added to the culture at a rate of from 0.5 to 2 gL-1h-1;
   f. the nitrogen source is added to the culture at a rate of from 0.4 to 1.5 gL" 1h-1;
   g. an inducer concentration of at least 0.1 mM and no more than 0.5 mM wherein the inducer is IPTG (isopropyl thio-galacto-pyranoside);
   h. purifying the crude recombinant lectin protein using at least one chromatography step,
   wherein by carrying out the induction phase under conditions e.g., resulting in a doubling time of 100 to 160 hours, cleavage of the initiator methionine is catalysed to reduce methionine residue in the recombinant lectin protein, and obtain a recombinant lectin protein in which less than 20% of recombinant lectin includes the initiator methionine.

2. The method as claimed in claim 1, wherein the host cell culture has a volume of at least 10L.

3. The method according to claim 1, wherein the method comprises culturing the host cell, said culturing comprising: a growth phase during which the host cell is grown prior to protein expression; and an expression phase during which protein expression is performed, wherein the growth phase is carried out at a temperature which is greater than the temperature at which the expression phase is performed, and wherein the temperature is reduced from the growth phase to the expression phase over a period of at least 4 and no more than 7 hours.

4. The method as claimed in claim 1, wherein the method further comprises:
   a) optionally, cloning a recombinant lectin gene into an expression vector and inserting the expression vector into a host cell;
   b) culturing the host cell in a suitable medium, wherein said culturing comprises a growth phase which is carried out at a temperature of from 25° C. to 40° C., and an expression phase during which the recombinant lectin protein encoded by the recombinant lectin gene is expressed;
   c) optionally, isolating the recombinant lectin protein expressed in (b) to obtain a crude recombinant lectin protein by centrifugation followed by disruption of cell surface; and
   d) optionally, purifying the crude recombinant lectin protein to obtain a recombinant lectin protein isolate.

5. The method as claimed in claim 4, step 'b', wherein the carbon source is glucose or glycerol, and wherein the nitrogen source is tryptone, peptone or yeast extract.

6. The method as claimed in claim 4, wherein the nitrogen source is tryptone, peptone or yeast extract.

7. The method as claimed in claim 4, wherein isolating a crude recombinant lectin protein in step 'd' is carried out by centrifugation followed by disruption of cell surface.

8. The method as claimed in claim 4, wherein purifying the crude recombinant lectin protein in step 'd' comprises atleast one chromatographic step selected from anion exchange chromatography, cation exchange chromatography or hydrophobic interaction chromatography.

9. The method as claimed in claim 8, wherein at least one chromatographic step comprises anion exchange chromatography and/or cation exchange chromatography.

10. The method as claimed in claim 8, wherein the at least one chromatographic step comprises hydrophobic interaction chromatography.

11. The method as claimed in claim 4, wherein purifying the crude recombinant lectin protein in step 'e''d)' comprises a filtration step.

12. The method as claimed in claim 4, wherein the host cell culture has a volume of at least 10L.

13. The method of purifying a crude recombinant lectin protein as claimed in claim 1 comprising:
   a) initial purification of the crude recombinant lectin protein by anion exchange chromatography to obtain a first purified elute;
   b) optional purification of the first purified elute by hydrophobic interaction chromatography to obtain a second purified elute;
   c) optional purification of the second purified elute by cation exchange chromatography to obtain a third purified elute;
   d) further purification of the first, second or third purified elute by anion exchange chromatography to obtain a fourth purified elute; and
   e) buffer exchange of the fourth purified elute by diafiltration to obtain a purified recombinant lectin protein isolate.

\* \* \* \* \*

```
                        SEQUENCE LISTING

<160> NUMBER OF SEQ ID NOS: 5

<210> SEQ ID NO 1
<211> LENGTH: 141
<212> TYPE: PRT
<213> ORGANISM: Artificial Sequence
<220> FEATURE:
<223> OTHER INFORMATION: In vitro

<400> SEQUENCE: 1

Thr Tyr Lys Ile Thr Val Arg Val Tyr Gln Thr Asn Pro Asp Ala Phe
1               5                  10                  15

Phe His Pro Val Glu Lys Thr Val Trp Lys Tyr Ala Asn Gly Gly Thr
                20                  25                  30

Trp Thr Ile Thr Asp Asp Gln His Val Leu Thr Met Gly Gly Ser Gly
            35                  40                  45

Thr Ser Gly Thr Leu Arg Phe His Ala Asp Asn Gly Glu Ser Phe Thr
        50                  55                  60

Ala Thr Phe Gly Val His Asn Tyr Lys Arg Trp Cys Asp Ile Val Thr
65                  70                  75                  80

Asn Leu Ala Ala Asp Glu Thr Gly Met Val Ile Asn Gln Gln Tyr Tyr
                85                  90                  95

Ser Gln Lys Asn Arg Glu Glu Ala Arg Glu Arg Gln Leu Ser Asn Tyr
            100                 105                 110

Gln Val Lys Asn Ala Lys Gly Arg Asn Phe Gln Ile Val Tyr Thr Glu
        115                 120                 125

Ala Glu Gly Asn Asp Leu His Ala Asn Leu Ile Ile Gly
    130                 135                 140

<210> SEQ ID NO 2
<211> LENGTH: 141
<212> TYPE: PRT
<213> ORGANISM: Artificial Sequence
<220> FEATURE:
<223> OTHER INFORMATION: In vitro

<400> SEQUENCE: 2

Thr Tyr Lys Ile Thr Val Arg Val Tyr Gln Thr Asn Pro Asn Ala Phe
1               5                  10                  15

Phe His Pro Val Glu Lys Thr Val Trp Lys Tyr Ala Asn Gly Gly Thr
                20                  25                  30

Trp Thr Ile Thr Asp Asp Gln His Val Leu Thr Met Gly Gly Ser Gly
            35                  40                  45

Thr Ser Gly Thr Leu Arg Phe His Ala Asp Asn Gly Glu Ser Phe Thr
        50                  55                  60

Ala Thr Phe Gly Val His Asn Tyr Lys Arg Trp Cys Asp Ile Val Thr
65                  70                  75                  80

Asn Leu Ala Ala Asp Glu Thr Gly Met Val Ile Asn Gln Gln Tyr Tyr
                85                  90                  95

Ser Gln Lys Asn Arg Glu Glu Ala Arg Glu Arg Gln Leu Ser Asn Tyr
            100                 105                 110

Glu Val Lys Asn Ala Lys Gly Arg Asn Phe Gln Ile Val Tyr Thr Glu
        115                 120                 125

Ala Glu Gly Asn Asp Leu His Ala Asn Leu Ile Ile Gly
    130                 135                 140
```

```
<210> SEQ ID NO 3
<211> LENGTH: 141
<212> TYPE: PRT
<213> ORGANISM: Artificial Sequence
<220> FEATURE:
<223> OTHER INFORMATION: In vitro

<400> SEQUENCE: 3

Val Tyr Lys Ile Thr Val Arg Val Tyr Gln Thr Asn Pro Asp Ala Phe
1               5                   10                  15

Phe His Pro Val Glu Lys Thr Val Trp Lys Tyr Ala Asn Gly Gly Thr
                20                  25                  30

Trp Ser Ile Thr Asp Asp Gln His Val Leu Thr Met Gly Gly Ser Gly
            35                  40                  45

Thr Ser Gly Thr Leu Arg Phe His Ala Asp Asn Gly Glu Ser Phe Thr
        50                  55                  60

Ala Thr Phe Gly Val His Asn Tyr Lys Arg Trp Cys Asp Ile Val Thr
65                  70                  75                  80

Asn Leu Ala Ala Asp Glu Thr Gly Met Val Ile Asn Gln Gln Tyr Tyr
                85                  90                  95

Ser Gln Lys Asn Arg Glu Glu Ala Arg Glu Arg Gln Leu Ser Asn Tyr
                100                 105                 110

Gln Val Lys Asn Ala Lys Gly Arg Asn Phe Gln Ile Val Tyr Thr Glu
            115                 120                 125

Ala Glu Gly Asn Asp Leu His Ala Asn Leu Ile Ile Gly
        130                 135                 140

<210> SEQ ID NO 4
<211> LENGTH: 141
<212> TYPE: PRT
<213> ORGANISM: Artificial Sequence
<220> FEATURE:
<223> OTHER INFORMATION: In vitro

<400> SEQUENCE: 4

Val Tyr Lys Ile Thr Val Arg Val Tyr Gln Thr Asn Pro Asp Ala Phe
1               5                   10                  15

Phe His Pro Val Glu Lys Thr Val Trp Lys Tyr Ala Asp Gly Gly Thr
                20                  25                  30

Trp Ser Ile Thr Asp Asp Gln His Val Leu Thr Met Gly Gly Ser Gly
            35                  40                  45

Thr Ser Gly Thr Leu Arg Phe His Ala Asp Asn Gly Glu Ser Phe Thr
        50                  55                  60

Ala Thr Phe Gly Val His Asp Tyr Lys Arg Trp Cys Asp Ile Val Thr
65                  70                  75                  80

Asp Leu Ala Ala Asp Glu Thr Gly Met Val Ile Asn Gln Glu Tyr Tyr
                85                  90                  95

Ser Glu Lys Asp Arg Glu Glu Ala Arg Glu Arg Gln Asn Ser Asn Tyr
                100                 105                 110

Glu Val Lys Asp Ala Lys Gly Arg Asn Phe Glu Ile Val Tyr Thr Glu
            115                 120                 125

Ala Glu Gly Asn Asp Leu His Ala Asp Leu Ile Ile Gly
        130                 135                 140

<210> SEQ ID NO 5
<211> LENGTH: 426
<212> TYPE: DNA
<213> ORGANISM: Artificial Sequence
```

```
<220> FEATURE:
<223> OTHER INFORMATION: In vitro

<400> SEQUENCE: 5
atgacctata aaattaccgt gcgcgtgtat cagaccaacc cggatgcctt tttccatccg      60
gtggaaaaaa ccgtgtggaa atatgcgaat ggcggtacct ggacgattac ggatgatcag     120
catgtgctga cgatgggtgg tagcggtacc agcggcaccc tgcgttttca cgcagataat     180
ggcgaaagct tcaccgccac ctttggtgtg cataattata aacgctggtg tgatattgtg     240
accaacctgg cagcggatga aaccggcatg gttattaatc agcagtatta tagtcagaaa     300
aaccgcgaag aagcgcgtga acgccagctg agtaactatc aggtgaaaaa tgcgaaaggc     360
cgtaacttcc agattgttta taccgaagcg gaaggcaatg atctgcatgc gaacctgatt     420
atcggc                                                                426
```